US009415059B2

(12) United States Patent
Kato et al.

(10) Patent No.: US 9,415,059 B2
(45) Date of Patent: Aug. 16, 2016

(54) PARTICULATE COMPOSITION AND PHARMACEUTICAL COMPOSITION CONTAINING THE SAME

(75) Inventors: Yasuki Kato, Kashiwa (JP); Atsushi Ishii, Kashiwa (JP)

(73) Assignee: Nanocarrier Co., Ltd., Kashiwa (JP)

( * ) Notice: Subject to any disclaimer, the term of this patent is extended or adjusted under 35 U.S.C. 154(b) by 55 days.

(21) Appl. No.: 13/381,841

(22) PCT Filed: Aug. 31, 2010

(86) PCT No.: PCT/JP2010/064816
§ 371 (c)(1), (2), (4) Date: Dec. 30, 2011

(87) PCT Pub. No.: WO2011/025036
PCT Pub. Date: Mar. 3, 2011

(65) Prior Publication Data

US 2012/0107377 A1 May 3, 2012

(30) Foreign Application Priority Data

Aug. 31, 2009 (JP) ................................ 2009-200681

(51) Int. Cl.

| | |
|---|---|
| ***A61K 38/16*** | (2006.01) |
| ***A61K 31/7088*** | (2006.01) |
| ***A61K 9/107*** | (2006.01) |
| ***A61K 9/127*** | (2006.01) |
| ***A61K 31/715*** | (2006.01) |
| ***A61K 38/38*** | (2006.01) |
| ***C12N 15/88*** | (2006.01) |

(52) U.S. Cl.
CPC ............ *A61K 31/7088* (2013.01); *A61K 9/107* (2013.01); *A61K 9/1271* (2013.01); *A61K 9/1272* (2013.01); *A61K 31/715* (2013.01); *A61K 38/38* (2013.01); *C12N 15/88* (2013.01)

(58) Field of Classification Search
CPC .................................................. A61K 9/1271
See application file for complete search history.

(56) References Cited

U.S. PATENT DOCUMENTS

| | | | | |
|---|---|---|---|---|
| 5,449,513 | A | 9/1995 | Yokoyama et al. | |
| 5,510,103 | A | 4/1996 | Yokoyama et al. | |
| 6,328,979 | B1 | 12/2001 | Yamashita et al. | |
| 6,383,811 | B2 | 5/2002 | Wolff et al. | |
| 6,919,372 | B1 | 7/2005 | Yamashita et al. | |
| 2003/0191081 | A1 | 10/2003 | Lemieux et al. | |
| 2004/0253315 | A1* | 12/2004 | Ogawa et al. | 424/490 |
| 2006/0025366 | A1 | 2/2006 | MacLachlan et al. | |
| 2006/0051405 | A1 | 3/2006 | MacLachlan et al. | |
| 2006/0093557 | A1* | 5/2006 | Dickinson et al. | 424/46 |
| 2007/0071823 | A1* | 3/2007 | Wolff et al. | 424/484 |
| 2009/0258079 | A1 | 10/2009 | Katakai et al. | |
| 2009/0291130 | A1 | 11/2009 | Ohuchi et al. | |
| 2011/0268772 | A1* | 11/2011 | Kim et al. | 424/400 |

FOREIGN PATENT DOCUMENTS

| | | | | |
|---|---|---|---|---|
| EP | 1 230 934 A1 | 8/2002 | | |
| EP | 1 731 173 A1 | 12/2006 | | |
| EP | 2 077 293 A1 | 7/2009 | | |
| EP | 2 157 096 A1 | 2/2010 | | |
| JP | 6-107565 | 4/1994 | | |
| JP | 2001-504093 | 3/2001 | | |
| JP | 2001-510786 | 8/2001 | | |
| JP | 2005-519063 | 6/2005 | | |
| JP | 2006-56864 | 3/2006 | | |
| JP | 2008-504827 | 2/2008 | | |
| WO | WO 98/16202 | 4/1998 | | |
| WO | WO 98/58630 | 12/1998 | | |
| WO | WO 99/04761 | 2/1999 | | |
| WO | WO 99/33489 | 7/1999 | | |
| WO | WO 01/34115 A2 | 5/2001 | | |
| WO | WO 2005/007196 A2 | 1/2005 | | |
| WO | WO 2005/026372 A1 | 3/2005 | | |
| WO | WO 2005/092389 A1 | 10/2005 | | |
| WO | WO 2006/002538 A1 | 1/2006 | | |
| WO | WO 2006/085664 A1 | 8/2006 | | |
| WO | WO 2007/043486 A1 | 4/2007 | | |
| WO | WO 2007/136134 A1 | 11/2007 | | |
| WO | WO 2008/010341 A1 | 1/2008 | | |
| WO | WO 2008/042973 A2 | 4/2008 | | |
| WO | WO 2008/047948 A1 | 4/2008 | | |
| WO | WO 2008/143339 A1 | 11/2008 | | |
| WO | WO 2010074540 A2 * | 7/2010 | ............... | A61K 9/00 |

OTHER PUBLICATIONS

International Search Report, dated Sep. 28, 2010, corresponding to PCT/JP2010/064816, 5 pages.

Extended European Search Report issued in corresponding European Patent Application No. 10812082.5, dated Oct. 28, 2013, 10pp. (citing all of the identified documents, see all pages).

Read, Martin L. et al.; "A versatile reducible polycation-based system for efficient delivery of a broad range of nucleic acids"; Nucleic Acids Research; May 24, 2005; vol. 33; No. 9; e86; 16pp.

European Office action dated Jan. 22, 2016 for corresponding European Application No. 10 812 082.5, 5pp.

* cited by examiner

*Primary Examiner* — Kyle Purdy
(74) *Attorney, Agent, or Firm* — Lewis Roca Rothgerber Christie LLP

(57) ABSTRACT

The present invention provides a particulate composition containing: block copolymer units being arranged radially with hydrophobic polymer-chain segments radially inside and hydrophilic polymer-chain segments radially outside; and a charged lipid which carries a charge opposite to the charge of a drug to be encapsulated, the charged lipid being attracted to the hydrophobic polymer-chain segment. In this particulate composition, the drug is retained within the particle via electrostatic binding with the charged lipid, whereby the outer surface of the particle is prevented from being charged to attract a substance which has a charge opposite to that of the charged lipid.

8 Claims, 6 Drawing Sheets

(a)

(b)

(c)

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial
<220> FEATURE:
<223> OTHER INFORMATION: a sense strand of a double-strand siRNA
      designed to target Firefly luciferase gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine
```

-continued

```
<400> SEQUENCE: 1

cuuacgcuga guacuucgan n                                               21


<210> SEQ ID NO 2
<211> LENGTH: 21
<212> TYPE: RNA
<213> ORGANISM: Artificial
<220> FEATURE:
<223> OTHER INFORMATION: an antisense strand of a double-strand siRNA
      designed to target firefly luciferase gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 2

ucgaaguacu cagcguaagn n                                               21


<210> SEQ ID NO 3
<211> LENGTH: 21
<212> TYPE: RNA
<213> ORGANISM: Artificial
<220> FEATURE:
<223> OTHER INFORMATION: a sense strand of a double-strand siRNA
      designed to target Human Polo-like kinase 1 gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 3

ccauuaacga gcugcuuaan n                                               21


<210> SEQ ID NO 4
<211> LENGTH: 21
<212> TYPE: RNA
<213> ORGANISM: Artificial
<220> FEATURE:
<223> OTHER INFORMATION: an antisense strand of a double-strand siRNA
      designed to target Human Polo-like kinase 1 gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 4

uuaagcagcu cguuaauggn n                                               21
```

PARTICULATE COMPOSITION AND PHARMACEUTICAL COMPOSITION CONTAINING THE SAME

CROSS-REFERENCE TO RELATED APPLICATION

This application is a National Phase Patent Application and claims the priority of International Application Number PCT/JP2010/064816, filed on Aug. 31, 2010, which claims priority of Japanese Patent Application Number 2009-200681, filed on Aug. 31, 2009.

INCORPORATION BY REFERENCE

The material in the text file entitled "SequenceListing.txt", created/amended Dec. 29, 2011 and being 1,982 bytes, is herein incorporated by reference in its entirety.

TECHNICAL FIELD

The present invention relates to a particulate composition (such as a polymeric micelle) applicable for a carrier of a drug delivery system (DDS), and to a pharmaceutical composition (such as a polymeric micelle formulation) containing a drug encapsulated in the particulate composition.

BACKGROUND ART

Biotechnology-based pharmaceuticals, which utilize biomacromolecules such as proteins and nucleic acids, are more susceptible to enzymatic degradation or immune elimination, compared with conventional pharmaceuticals based on low-molecular compounds. Patent Documents 1 to 4 disclose a DDS which contains a biomacromolecule within a liposome made of a lipid bilayer membrane, which intends to improve the in vivo stability of biotechnology-based pharmaceuticals.

PRIOR ART REFERENCES

Patent Documents

Patent Document 1: WO2001/034115
Patent Document 2: WO1998/58630
Patent Document 3: WO2005/092389
Patent Document 4: JP2001-504093W

DISCLOSURE OF THE INVENTION

Problems to be Solved by the Invention

The conventional DDSs described in Patent Documents 1 to 3, in which the biomacromolecule drug is protected with a lipid bilayer membrane, are superior in in vivo stability of the drug, but are inferior in drug releasability from the carrier. In addition, due to the large particle size and also due to the electrical charge of the lipid which constitutes the lipid bilayer membrane, the conventional DDSs are likely to be captured by the reticuloendothelial system, such as the lungs, liver and spleen, and thereby removed from blood before reaching to the administration target. The DDS described in Patent Document 4 is a "stealth" liposome and prevented from being captured by the reticuloendothelial system, but tends to have difficulty in releasing the drug from the carrier.

A polymeric micelle formed with a block copolymer unit having a hydrophobic polymer-chain segment and a hydrophilic polymer-chain segment can be used as a DDS carrier, and the resultant DDS can be much smaller in particle size (e.g., the average particle size can be 100 nm or smaller) than the conventional DDSs using a liposome. However, such a DDS using a polymeric micelle as the carrier still has difficulty, in some cases, in delivering the drug to the administration target, due to lack of sufficient encapsulation force to maintain the biomacromolecule within the DDS particle as shown in the Comparative Examples, which will be explained later. In addition, such a DDS may sometimes cause the drug to disengage from the carrier during the storage period after production.

Means to Solve the Problems

The present invention provides a particulate composition containing: a block copolymer unit having a hydrophobic polymer-chain segment and a hydrophilic polymer-chain segment, a plurality of the block copolymer units being arranged radially with the hydrophobic polymer-chain segments radially inside and the hydrophilic polymer-chain segments radially outside; and a charged lipid which carries a charge opposite to the charge of a drug to be encapsulated in the composition such that the drug is to be retained within the particle via electrostatic binding with the charged lipid, the charged lipid being attracted to the hydrophobic polymer-chain segment, whereby the outer surface of the particle is prevented from being charged to attract a substance which has a charge opposite to the charge of the charged lipid.

In another aspect, the present invention provides a pharmaceutical composition containing the particulate composition and a drug which carries a charge opposite to the charge of the charged lipid and is encapsulated in the particulate composition.

Effects of the Invention

The present invention provides a drug carrier which has improved drug encapsulation stability and is prevented from adhesion of a biomolecule onto the carrier surface, which may obstruct delivery of a drug to a desired target, being suitable for DDS, as well as a pharmaceutical composition using the drug carrier. The drug carrier and pharmaceutical composition can deliver the drug more reliably than the conventional DDSs.

BRIEF DESCRIPTION OF THE DRAWINGS

FIG. 4 illustrates the results of electrophoresis in Evaluation 5a;

DESCRIPTION OF EMBODIMENTS

Figure 1:
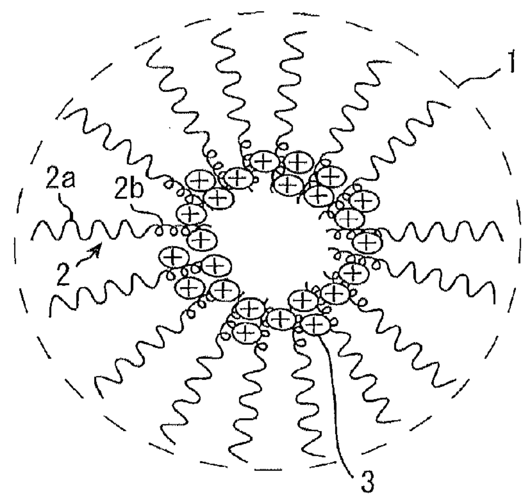
FIGS. 1(*a*) to 1(*c*) illustrate structural examples for a particulate composition and a pharmaceutical composition according to the present invention.
Figure 1:
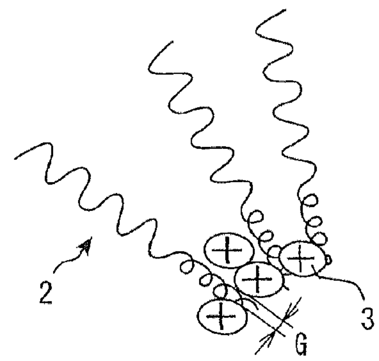
Figure 1:
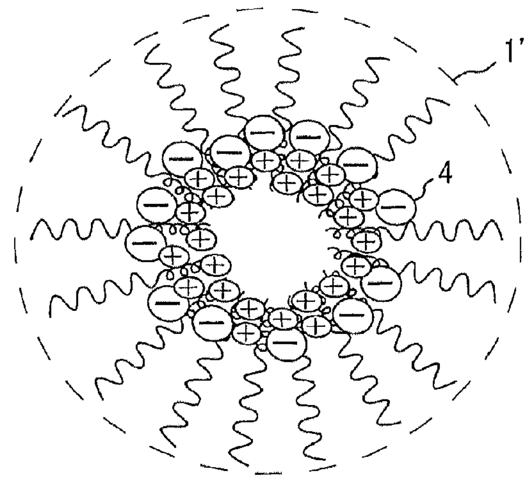

FIG. 1(*a*) illustrates a structural example of a particulate composition according to the present invention (hereinafter also referred to as "particulate composition"), and FIG. 1(*b*) is a partial enlarged view thereof. The particulate composition 1 contains a block copolymer unit 2 and a charged lipid 3. The block copolymer unit 2 has a hydrophilic polymer-chain segment 2*a* and a hydrophobic polymer-chain segment 2*b*. The block copolymer units 2 are arranged radially in the particulate composition 1 with the hydrophobic polymer-chain segments 2*b* radially inside and the hydrophilic polymer-chain segments 2*a* radially outside. The charged lipid 3 carries a charge opposite to the charge of a drug to be encapsulated, and is being attracted to the hydrophobic polymer-chain segments 2*b*. FIG. 1(*c*) illustrates a structural example of a particulate pharmaceutical composition according to the present invention (hereinafter also referred to as "pharmaceutical composition"). A pharmaceutical composition 1' includes a particulate composition 1 and a drug 4, which carries a charge opposite to the charge of a charged lipid 3 and is retained within the particulate composition 1 via electrostatic binding with the charged lipid 3.

The term "charged lipid" as used herein means either an anionic lipid, which has more negative charges than positive charges in an aqueous medium, or a cationic lipid, which has more positive charges than negative charges in an aqueous medium. Amphoteric lipids, which have both cationic groups and anionic groups, are judged by the aforementioned criteria.

The charged lipid 3 retains the drug 4 to be encapsulated within the particulate composition 1 via electrostatic binding. The charged lipid 3 only needs to have an electrical charge opposite to the charge of the drug 4 to be encapsulated at least under storage environment of the pharmaceutical composition 1' formed from the particulate composition 1. This will allow the drug 4 to be retained more securely in the particulate composition 1 during the storage period after production. The charged lipid 3 and the drug 4 should preferably have charges opposite to each other even under physiological environments, such as in blood (e.g., pH 7.4). This will enable more secure prevention of the drug 4 from disengaging from the particulate composition 1 during transport to the administration target.

The charged lipids 3 are being attracted to the hydrophobic polymer-chain segments 2*b* by the following mechanism. The particulate composition 1 is formed by a method including the step of suspending the block copolymer units 2 and the charged lipids 3 into an aqueous solution. The hydrophobic polymer-chain segments 2*b* of the block copolymer units 2 cannot disperse, but form an aggregate, in the aqueous solution due to their hydrophobicity, while the hydrophilic polymer-chain segments 2*a* can disperse, and move freely, in the aqueous solution. Thus, the block copolymer units 2 are arranged radially in the aqueous solution, with the hydrophobic polymer-chain segments 2*b* radially inside and the hydrophilic polymer-chain segments 2*a* radially outside. The charged lipids 3 are being attracted to the hydrophobic polymer-chain segments 2*b*, since they are highly hydrophobic and have higher affinity for the hydrophobic polymer-chain segments 2*b* than for water or the hydrophilic polymer-chain segments 2*a*. Thus, the charged lipids 3 are arranged away from the outer surface of the particulate composition 1. Thus, the outer surfaces of the particulate composition 1 and the pharmaceutical composition 1' are prevented from being charged to attract a substance which has a charge opposite to that of the charged lipids 3 (e.g., blood proteins).

When the charged lipids 3 and the block copolymer units 2 are suspended in the aqueous solution, they form particles in a mixture state, so that the charged lipids 3 adjacent to one another along the circumference of the particulate composition 1 are not contiguous with one another, but intervene between the adjacent block copolymer units 2 along the circumference of the particulate composition 1, as shown in FIG. 1(*b*). Thus, the adjacent charged lipids 3 along the circumference of the particulate composition 1 are separated by the block copolymer units 2, and prevented from being in contact with one another. Accordingly, in the particulate composition 1, gaps G sufficiently large to accommodate block copolymer units 2 are formed in between the adjacent charged lipids 3 along the circumference of the particulate composition 1. In other words, gaps G are formed in between the adjacent charged lipids 3, and the block copolymer units 2 are positioned within the gaps G. The binding force between the charged lipid 3 and the block copolymer unit 2 is smaller than that between the charged lipids 3. Therefore, compared to the conventional DDSs (liposomes) in which the lipids are arranged contiguously to each other along the circumference of the particle, the particulate composition 1 can disintegrate its particular shape easily due to disengagement of the charged lipids 3. As a result, the drug 4 encapsulated in the particles (carriers) is prevented from being retained excessively. On the other hand, stealth liposomes, represented by the DDSs described in Patent Document 4, are prepared by first forming liposomes with lipid bilayers and then attaching diblock copolymers to the surface of the liposomes, whereby the adjacent lipids along the circumference of the particle are not separated from one another by, e.g., the block copolymers, but are arranged contiguously to one another.

The state in which the outer surface of the particulate composition 1 or the pharmaceutical composition 1' is prevented from being charged to attract a charged substance can be confirmed based on, i.e., whether the absolute value of zeta potential of the particulate composition 1 or the pharmaceutical composition 1' is lower than a predetermined value. Specifically, the absolute value of zeta potential of the pharmaceutical composition 1' should preferably be 10 mV or lower, e.g. 5 mV or lower, or 3 mV or lower, more preferably 2 mV or lower, still more preferably 1 mV or lower. Incorporation of the drug 4 into the particulate composition 1 tends to reduce the absolute value of zeta potential of the resultant pharmaceutical composition 1' to be lower than the absolute value of zeta potential of the particulate composition 1. Accordingly, the absolute value of zeta potential of the particulate composition 1 should preferably be 15 mV or lower, e.g. 12 mV or lower, or 6 mV or lower, more preferably 3 mV or lower, preferably 2 mV or lower, still more preferably 1 mV or lower. The zeta potential can be measured by adding the particulate composition 1 or the pharmaceutical composition 1' to 10 mM HEPES buffer solution (pH 7.4) in such an amount that the ratio of the total charged lipids 3 to the buffer solution is 0.1 mg/mL.

Note that the absolute values of zeta potential mentioned herein may be rounded off to the nearest whole numbers. For example, the absolute value of zeta potential of "2 mV or lower" should cover values of less than 2.5 mV.

As demonstrated in the Examples below, aggregation of the particulate composition 1 or the pharmaceutical composition 1' in blood can be prevented by controlling the absolute value of zeta potential of the particulate composition 1 or the pharmaceutical composition 1' to a low level. Specifically, if the absolute value of zeta potential of the particulate composition 1 is controlled to be lower than a predetermined value, aggregation in blood can be prevented to such a degree that the aggregability of the particulate composition 1 in blood should preferably be, e.g., 0.2 or lower, or 0.18 or lower, or 0.15 or lower, more preferably 0.1 or lower, or in some cases 0.05 or lower. Alternatively, by controlling the absolute value of zeta potential of the pharmaceutical composition 1' to be lower than a predetermined value, aggregation in blood can be prevented to such a degree that the aggregability of the pharmaceutical composition 1' in blood should preferably be, e.g., 0.2 or lower, or 0.16 or lower, more preferably 0.1 or lower, or in some cases 0.05 or lower.

The aggregability in blood can be calculated as follows:

(i) Sample A is prepared by adding an object composition (particulate composition 1 or pharmaceutical composition 1') to 10 mM HEPES buffer solution (pH 7.4) in such an amount that the ratio of the total charged lipids 3 to the buffer solution is 2.2 mg/mL, followed by addition of 9 mL of FBS (fetal bovine serum) per mL of the buffer solution.

(ii) Sample B is prepared in a similar manner to step (i) above, except that the FBS (fetal bovine serum) is replaced with 10 mM HEPES buffer solution (pH 7.4).

(iii) Samples A and B are let stand at 37° C. for 24 hours, after which the absorbance at a wavelength of 700 nm is measured for each sample.

(iv) The "absorbance for Sample B" is subtracted from the "absorbance for Sample A," and the resultant value is determined as the aggregability in blood. The smaller the value is, the less likely to aggregate in blood the object composition is.

The ratio by weight of the amount of the block copolymer units 2 to the amount of the charged lipids 3 should preferably be 1.0 or higher, more preferably 1.5 or higher, still more preferably 2.0 or higher, and preferably 50 or lower, more preferably 20 or lower, still more preferably 10 or lower. The higher the ratio, the lower the absolute value of zeta potential of the particulate composition 1 or the pharmaceutical composition 1'. Drugs 4 can be encapsulated more actively into the particle as the ratio of the charged lipids 3 becomes higher, for which reason the ratio should preferably be limited to 50 or lower, as mentioned above.

The lipids 3 may be a simple lipid, a conjugated lipid or a derived lipid. Examples thereof include phospholipids, glycoglycerolipids, glucosphingolipids, sphingoids and sterols. Specifically, examples of cationic lipids include 1,2-dioleoyl-3-trimethylammoniopropane (DOTAP), N-(2,3-dioleoyloxypropan-1-yl)-N,N,N-trimethylammonium chloride (DOTMA), 2,3-dioleoyloxy-N-[2-(sperminecarboxyamide)ethyl]-N,N-dimethyl-1-propanaminium trifluoroacetate (DOSPA), 1,2-dimyristyloxypropyl-3-dimethylhydroxyethylammonium bromide (DMRIE), 1,2-dioleoyloxypropyl-3-diethylhydroxyethylammonium bromide (DORIE), and 3β-[N—(N'N'-dimethylaminoethyl)carbamoyl]cholesterol (DC-Chol). Examples of anionic lipids include cardiolipin, diacylphosphatidylserine, diacylphosphatidic acid, N-succinyl phosphatidylethanolamine (N-succinyl PE), phosphatidic acid, phosphatidylinositol, phosphatidylglycerol, phosphatidylethylene glycol, and cholesterol succinate.

The hydrophilic polymer-chain segment **2*a* should preferably be a water-soluble polymer-chain segment made of polyethyleneglycol or polyoxyethylene. The molecular weight of the hydrophilic polymer-chain segment 2*a* should preferably be 2,500 Da or higher, more preferably 5,000 Da or higher, still more preferably 8,000 Da or higher, and preferably 200,000 Da or lower, more preferably 20,000 Da or lower, still more preferably 15,000 Da or lower. The hydrophobic polymer-chain segment 2*b* should preferably be a segment derived from a polyamino acid chain. The number of repeating units in the hydrophobic polymer-chain segment 2*b* should preferably be 10 or higher, more preferably 20 or higher, and preferably 200 or lower, more preferably 100 or lower, still more preferably 60 or lower. In order to reduce the absolute value of zeta potential of the particulate composition 1, i.e., to reduce the surface charge of the pharmaceutical composition 1' (to be closer to neutral), the size of the hydrophilic polymer-chain segment 2*a* (molecular weight) should preferably be larger than the size of the hydrophobic polymer-chain segment 2*b* (the number of repeating units) in the block copolymer unit 2**.

The hydrophilic polymer-chain segment **2*a* and the hydrophobic polymer-chain segment 2*b* may also have a charged substituent such as an amino group and carboxy group, as long as the outer surface of the particulate composition 1 or the pharmaceutical composition 1'** does not bear a charge which can attract a charged substance.

The hydrophilic polymer-chain segment **2*a* and the hydrophobic polymer-chain segment 2*b* can be linked to each other by covalently binding the termini of their main chains. Specifically, examples of the block copolymer unit 2 are the compounds represented by general formulae (I) and (II). The particulate composition 1 may contain two or more kinds of the block copolymer units 2**.

[Formula 1]

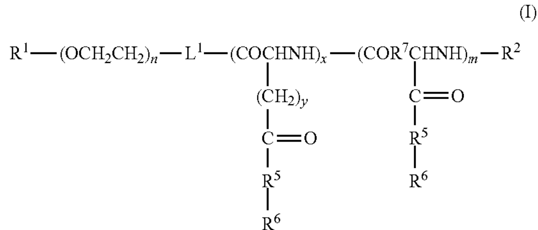

[Formula 2]

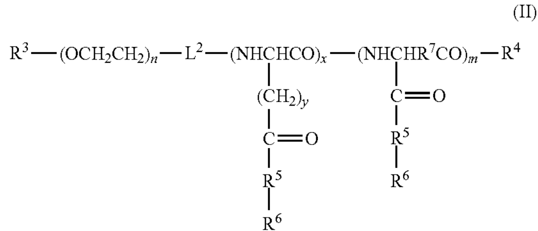

In formulae (I) and (II), $R^1$ and $R^3$, independently of each other, is either hydrogen atom or a group represented by $R^8(R^9)CH(CH_2)_q$—, where $R^8$ and $R^9$ (i) independently of each other, is hydrogen atom, $C_{1-6}$ alkoxy group, aryloxy group, aryl-$C_{1-3}$-oxy group, cyano group, carboxy group, amino group, $C_{1-6}$-alkoxy carbonyl group, $C_{2-7}$-acylamide group, tri-$C_{1-6}$-alkyl siloxy group, siloxy group, or silylamino group, (ii) together with each other, form ethylene dioxy group or propylene dioxy group, which are either unsubstituted or substituted with $C_{1-3}$-alkyl group, or (iii) together with CH group to which they are bound, form formyl group, and q is an integer of from 0 to 10;

$R^2$ is hydrogen atom, saturated or unsaturated $C_1$-$C_{29}$ aliphatic carbonyl group, or arylcarbonyl group;

$R^4$ is hydroxy group, saturated or unsaturated $C_1$-$C_{30}$-aliphatic oxy group, or aryl-lower-alkyloxy group;

$R^5$ is —O— or —NH—;

$R^6$ is hydrogen atom, phenyl group, benzyl group, —$(CH_2)_4$-phenyl group, $C_4$-$C_{16}$ alkyl group which is either unsubstituted or substituted with amino group or carbonyl group, or sterol derivative residue;

$R^7$ is methylene group;

n is an integer of from 55 to 4,600;

x is an integer of from 10 to 200;

m is an integer of from 0 to 200, wherein when m is one or more, the (COCHNH) units and the ($COR^7CHNH$) unit(s) may be arranged in a random order in the block copolymer, and when m is two or more, $R^6$ is selected for each amino acid unit independently of each other and may be arranged in a random order in the block copolymer, provided that hydrogen atoms must not exceed 75% of $R^6$;

y is 1 or 2;

$L^1$ is a linking group selected from —NH—, —O—, —O—Z—NH—, —CO—, —$CH_2$—, and —O—Z—S—Z—NH—, where Z, independently of each other, is $C_1$-$C_6$ alkylene group; and $L^2$ is a linking group selected from —OCO—Z—CO— and —NHCO—Z—CO—, where Z is $C_1$-$C_6$ alkylene group.

In formulae (I) and (II), n is an integer of preferably 110 or larger, more preferably 180 or larger, and preferably 460 or smaller, more preferably 340 or smaller;

x is an integer of preferably 20 or larger, and preferably 100 or smaller, more preferably 60 or smaller; and m is an integer of preferably 100 or smaller, more preferably 60 or smaller.

The block copolymer unit 2 may preferably be an anionic polymer. Use of an anionic polymer as the block copolymer unit 2 together with a cationic lipid as the charged lipid 3 makes it easier to control the absolute value of zeta potential of the particulate composition 1 and the pharmaceutical composition 1' at 3 mV or less, preferably 2 mV or less, and more preferably 1 mV or less. Also, as demonstrated in the Examples below, use of an anionic polymer as the block copolymer unit 2 makes it possible to prevent aggregation in blood more markedly, compared to the case where a neutral polymer having a similar absolute value of zeta potential is used. As used herein, polymers which have more negative charges than positive charges in an aqueous medium with a physiological pH (e.g., pH7.4) are regarded as anionic, polymers which have more positive charges than negative charges in the aqueous medium are regarded as cationic, and polymers which have substantially equal amounts of positive charges and negative charges in the aqueous medium are regarded as neutral.

Preferred examples of the anionic block copolymer unit 2 are compounds represented by general formulae (I) and (II) in which $R^5$ is —O—, $R^6$ is benzyl group, —$(CH_2)_4$-phenyl group, or $C_4$-$C_{16}$ alkyl group which is either unsubstituted or substituted with amino group or carbonyl group.

The block copolymer unit 2 can be formed, e.g., by coupling a polymer having a hydrophilic polymer chain with a polymer having a polyamino acid chain in a known manner, optionally after purifying, if necessary, the polymers to restrict the molecular weight distribution. The block copolymer unit 2 according to formula (I) also can be formed, e.g., by the steps of: performing anion living polymerization using an initiator which can add $R^1$ to form a polyethyleneglycol chain; introducing an amino group to the growing end; and polymerizing, at the amino end, an N-carboxy anhydride (NCA) of a protected amino acid, such as N$\epsilon$-Z-L-lysin, $\beta$-benzyl-L-aspartate, or $\gamma$-benzyl-L-glutamate.

The particulate composition 1 can be formed, e.g., as follows. First, a block copolymer unit 2 and a charged lipid 3, optionally together with a neutral lipid, are fully dissolved or dispersed into a forming solution containing an organic solvent, after which the organic solvent is removed by evaporation. Examples of organic solvents include acetone, dichloromethane, dimethylformamide, dimethylsulfoxide, acetonitrile, tetrahydrofuran, and methanol. The forming solution may contain two or more organic solvents, and also may contain a small amount of water. The resultant solid or paste is combined with water or an aqueous solution containing an additive such as an appropriate salt or stabilizer, followed by stirring to disperse the block copolymer unit and the lipid(s). The resultant product is further dispersed/pulverized by means of, e.g., ultrasonic irradiation, high-pressure emulsification or extruder to thereby form the particulate composition 1.

The present invention can provide a pharmaceutical composition 1' having the above particulate composition 1 and a drug 4 carrying a charge opposite to the charge of the charged lipid 3 contained in the particulate composition 1. The drug 4 is retained in the particulate composition 1 via electrostatic binding with the charged lipid 3. Thus, the binding between the charged lipid 3 and the drug 4 is reversible, and does not involve any chemical structural change. The drug 4 can be encapsulated into the carrier composition either by adding the drug 4 to the forming solution in the production of the carrier composition, or by adding the carrier composition to a solution of the drug 4.

Examples of the drug 4 include: anionic compounds, which have more negative charges than positive charges in an aqueous medium with a physiological pH (e.g., pH7.4); and cationic compounds, which have more positive charges than negative charges in the aqueous medium. The compounds should preferably be macromolecular compounds.

Examples of the macromolecular compounds that can be used as the drug 4 include peptides, proteins, sugar chains, and nucleic acids.

In order to prevent the drug 4 either from disengaging from the particulate composition 1 in blood too early or from being encapsulated in the particulate composition 1 for too long a time, the charge ratio between the charged lipid 3 and the drug 4 in the pharmaceutical composition 1' should preferably be controlled to be within a particular range. When the drug 4 is, e.g., a nucleic acid, the charge ratio can be defined as [the mol concentration of cationic groups of the charged lipid 3 contained in the particulate composition]/[the mol concentration of phosphoric groups in the nucleic acid]. On the other hand, when the drug is a compound which has both anionic and cationic groups, e.g., a protein, the charge ratio can be defined as [the mol concentration of charged groups of the charged lipid contained in the particulate composition]/([the mol concentration of groups in the drug which are charged oppositely to the charged lipid]−[the mol concentration of groups in the drug which are charged similarly to the charged lipid]). The charge ratio should preferably be 0.5 or higher, more preferably one or higher, still more preferably 2 or higher, and preferably 50 or lower, more preferably 20 or lower, still more preferably 10 or lower.

The average particle sizes of the particulate composition 1 and the pharmaceutical composition 1' should preferably be 10 nm or larger, more preferably 30 nm or larger, and preferably 300 nm or smaller, more preferably 200 nm or smaller.

EXAMPLES

The present invention will be explained in more detail below by referring to Examples. Measurement of the average particle sizes of particulate compositions by means of dynamic light scattering (DLS) mentioned in the following explanation was carried out using the light-scattering analyzer Zetasizer Nano ZS (Malvern Instruments).

Example Group 1

Particulate Composition

Example 1-1

Five grams of α-methoxy-ω-amino-polyethyleneglycol (hereinafter also referred to as "PEG") having a weight-average molecular weight (Mw) of 10000 (Manufactured by NOF Corp.) was dissolved into 50 mL of dimethyl sulfoxide, which was reacted with 5.5 g (42 parts with respect to polyethyleneglycol) of N-carboxy anhydride (NCA) of γ-benzyl-L-glutamate (hereinafter also referred to as "PBLG") at 40° C. for 24 hours. The reaction solution was dropped into 1 L of a mixture solvent of hexane and ethyl acetate (volume ratio 1:1) to cause precipitation of a polymer, which was recovered by filtration under reduced pressure and then dried to yield 8.6 g of a solid product. This product was dissolved into 86 mL of DMF, with which 432 μL of acetic anhydride was mixed and reacted at 40° C. for 24 hours. The reaction solution was dropped into 1 L of a mixture solvent of hexane and ethyl acetate (volume ratio 1:1) to cause precipitation of a polymer, which was recovered by filtration under reduced pressure and then further dried to yield 8.1 g of polyethyleneglycol-poly (γ-benzyl-L-glutamate)-Ac block copolymer (hereinafter also referred to as "PEG-PBLG"), which is a neutral polymer. The structural formula of PEG-PBLG is shown below. $^{1}$H-NMR analysis revealed that the degree of polymerization of the PBLG block was 40.

[Formula 3]

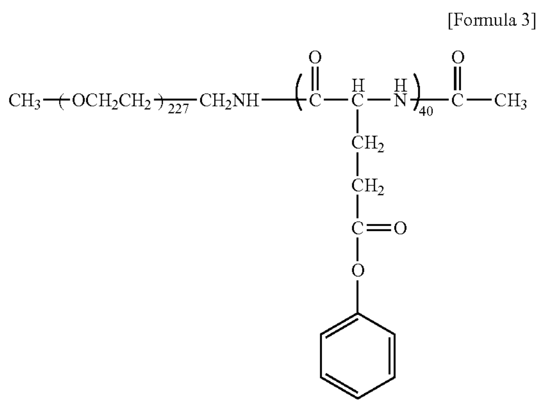

Four mL of the PEG-PBLG solution in chloroform (50 mg/mL) was mixed with 0.5 mL of 1,2-dioleoyl-3-trimethylammoniopropane (hereinafter also referred to as "DOTAP") (Avant Polar Lipid) solution in chloroform (40 mg/mL), the solvent was evaporated on a rotary evaporator, and was further dried overnight under reduced pressure. To the resulting solid, 10 mL of 20 mM HEPES buffer (pH7.4) was added, and stirred at room temperature for 3 hours to suspend the solid. The suspension was pulverized by ultrasonic irradiation (130 W, 1 second pulse, 20 minutes). The solution was passed through a 0.2 μm filter (Millex GP, Millipore) to thereby yield the particulate composition 1. The particulate composition 1 is formed with the hydrophobic polymer-chain segments arranged radially inside and the hydrophilic polymer-chain segments arranged radially outside. The particulate compositions 2 to 6 described below are also in a similar state.

Example 1-2

The particulate composition 2 was prepared in the same manner as in Example 1-1 except that DOTAP was replaced with phosphatidic acid (anionic charged lipid; hereinafter also referred to as "PA").

Example 1-3

Four mL of the PEG-PBLG solution in chloroform (50 mg/mL) prepared in Example 1-1 was mixed with 0.5 mL of the DOTAP (cationic lipid; Avant Polar Lipid) solution in chloroform (40 mg/mL) and 0.5 mL of dioleoylphosphatidylethanolamine (hereinafter also referred to as "DOPE"; Avant Polar Lipid) (neutral lipid; Avant Polar Lipid) solution in chloroform (40 mg/mL), the solvent was evaporated on a rotary evaporator, and was further dried overnight under reduced pressure. To the resulting solid, 5 mL of 20 mM HEPES buffer (pH7.4) was added, and stirred at room temperature for 3 hours to suspend the solid. The suspension was pulverized by ultrasonic irradiation (130 W, 1 second pulse, 20 minutes). The solution was passed through a 0.2 μm filter (Millex GP, Millipore) to thereby yield the particulate composition 3.

Example 1-4

The particulate composition 4 was prepared in the same manner as in Example 1-3 except that the amount of the chloroform solution of PEG-PBLG was changed to 2 mL.

Example 1-5

The particulate composition 5 was prepared in the same manner as in Example 1-3 except that the amount of the chloroform solution of PEG-PBLG was changed to 1.33 mL.

Example 1-6

The particulate composition 6 was prepared in the same manner as in Example 1-3 except that the amount of the chloroform solution of PEG-PBLG was changed to 1 mL.

Example 1-7

PEG-PBLG prepared in Example 1-1 was alkali-treated to deprotect the benzyl groups of the glutamic acid side chains, whereby polyethyleneglycol/poly(L-glutamic acid) block copolymer (PEG-pGlu) was prepared. The glutamic acid side chains of PEG-pGlu were partially modified with octyl groups ($C_8H_{17}$) via condensation reaction using octyl alcohol to thereby yield PEG-pGlu(C8) polymer, which is an anionic polymer. $^{1}$H-NMR analysis revealed that the number of octyl groups introduced was 33 per polymer. The structural formula of PEG-pGlu(C8) is shown below.

[Formula 4]

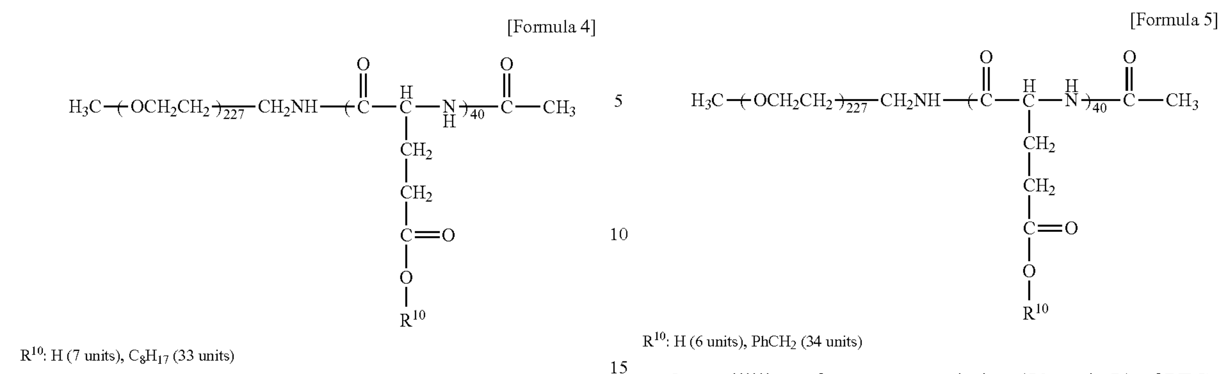

$R^{10}$: H (7 units), $C_8H_{17}$ (33 units)

[Formula 5]

$R^{10}$: H (6 units), $PhCH_2$ (34 units)

One milliliter of a methanol solution (50 mg/mL) of the resultant PEG-pGlu(C8) was mixed with 0.5 mL of a methanol solution (40 mg/mL) of DOTAP (cationic charged lipid; Avanti Polar Lipid) and 0.5 mL of a methanol solution (40 mg/mL) of dioleoylphosphatidylethanolamine (hereinafter also referred to as "DOPE") (neutral lipid; Avanti Polar Lipid), and then the solvent was evaporated on a rotary evaporator and dried overnight under reduced pressure. The resultant solid was combined with 2.5 mL of 100 mM sodium phosphate buffer (pH7.4), stirred for three hours at room temperature to obtain a suspension. The suspension was pulverized by ultrasonic irradiation (130 W, 1 second pulse, 10 minutes), and passed through a 0.2 μm filter (Millex GP, Millipore) to thereby yield the particulate composition 7.

Example 1-8

The particulate composition 8 was prepared in the same manner as in Example 1-7 except that the amount of the methanol solution (50 mg/mL) of PEG-pGlu (C8) was changed to 0.5 mL.

Example 1-9

PEG-PBLG prepared in Example 1-1 was alkali-treated to deprotect the benzyl groups of the glutamic acid side chains, whereby polyethyleneglycol/poly(L-glutamic acid) block copolymer (PEG-pGlu) was prepared. The glutamic acid side chains of PEG-pGlu were partially modified with benzyl groups ($PhCH_2$) via condensation reaction using benzyl alcohol to thereby yield PEG-pGlu(Bn), which is an anionic polymer. $^1$H-NMR analysis revealed that the number of benzyl groups introduced was 34 per polymer. The structural formula of PEG-pGlu(Bn) is shown below.

One milliliter of an acetone solution (50 mg/mL) of PEG-pGlu(C8) was mixed with 0.5 mL of a methanol solution (40 mg/mL) of DOTAP (cationic charged lipid; Avanti Polar Lipid) and 0.5 mL of a methanol solution (40 mg/mL) of dioleoylphosphatidylethanolamine (hereinafter also referred to as "DOPE") (neutral lipid; Avanti Polar Lipid), and then the solvent was evaporated on a rotary evaporator and dried overnight under reduced pressure. The resultant solid was combined with 2.5 mL of 100 mM sodium phosphate buffer (pH7.4), stirred for three hours at room temperature to obtain a suspension. The suspension was pulverized by ultrasonic irradiation (130 W, 1 second pulse, 10 minutes), and passed through a 0.2 μm filter (Millex GP, Millipore) to thereby yield the particulate composition 9.

Example 1-10

The particulate composition 10 was prepared in the same manner as in Example 1-7 except that the amount of the methanol solution of PEG-pGlu (C8) was changed to 0.5 mL.

Comparative Example 1-1

The comparative composition C1 was prepared in the same manner as in Example 1-1 except that no DOTAP was used.

Comparative Example 1-2

The comparative composition C2 was prepared in the same manner as in Example 1-3 except that no DOTAP was used.

Comparative Example 1-3

The comparative composition C3 was prepared in the same manner as in Example 1-3 except that no PEG-PBLG was used. The composition C3 does not contain a block copolymer but only contains DOTAP (charged lipid) and DOPE (neutral lipid).

[Evaluation 1a]

The average particle sizes of the particulate compositions 1 to 10 and the comparative particulate compositions C1 to C3 were measured using dynamic light scattering. The results are shown in Table 1.

TABLE 1

| | Particulate composition | Weight ratio of polymer and lipid | Particle size (nm) |
|---|---|---|---|
| Example 1-1 | 1 | PEG-PBLG:DOTAP = 10:1 | 64.7 |
| Example 1-2 | 2 | PEG-PBLG:PA = 10:1 | 73.2 |
| Example 1-3 | 3 | PEG-PBLG:DOTAP:DOPE = 10:1:1 | 88.7 |
| Example 1-4 | 4 | PEG-PBLG:DOTAP:DOPE = 5:1:1 | 90.3 |
| Example 1-5 | 5 | PEG-PBLG:DOTAP:DOPE = 3.3:1:1 | 87.7 |
| Example 1-6 | 6 | PEG-PBLG:DOTAP:DOPE = 2.5:1:1 | 88.1 |
| Example 1-7 | 7 | PEG-pGlu(C8):DOTAP:DOPE = 2.5:1:1 | 167.7 |
| Example 1-8 | 8 | PEG-pGlu(C8):DOTAP:DOPE = 1.25:1:1 | 158.1 |
| Example 1-9 | 9 | PEG-pGlu(Bn):DOTAP:DOPE = 2.5:1:1 | 137.1 |

TABLE 1-continued

| | Particulate composition | Weight ratio of polymer and lipid | Particle size (nm) |
|---|---|---|---|
| Example 1-10 | 10 | PEG-pGlu(Bn):DOTAP:DOPE = 1.25:1:1 | 158.1 |
| Comparative Example 1-1 | C1 | — | 94.2 |
| Comparative Example 1-2 | C2 | PEG-PBLG:DOPE = 10:1 | 87.3 |
| Comparative Example 1-3 | C3 | DOTAP:DOPE = 1:1 | 61.7 |

[Evaluation 1b]

To the particulate compositions 3 to 10 and the comparative particulate composition C3, 10 mM HEPES buffer (pH 7.4) was added to prepare samples having a charged lipid concentration of 0.1 mg/mL. Using the light-scattering analyzer Zetasizer Nano ZS (Malvern Instruments), the zeta potential for each sample (800 μL) was determined. Disposable capillary cells (DTS1060, Malvern Instruments) were used for measurement, and the temperature during measurement was set at 25° C.

TABLE 2

| Particulate composition | Weight ratio of polymer and lipid | Zeta potential (mV) |
|---|---|---|
| 3 | PEG-PBLG:DOTAP:DOPE = 10:1:1 | 2.04 |
| 4 | PEG-PBLG:DOTAP:DOPE = 5:1:1 | 5.38 |
| 5 | PEG-PBLG:DOTAP:DOPE = 3.3:1:1 | 7.80 |
| 6 | PEG-PBLG:DOTAP:DOPE = 2.5:1:1 | 11.0 |
| 7 | PEG-pGlu(C8):DOTAP:DOPE = 2.5:1:1 | 1.63 |
| 8 | PEG-pGlu(C8):DOTAP:DOPE = 1.25:1:1 | 1.09 |
| 9 | PEG-pGlu(Bn):DOTAP:DOPE = 2.5:1:1 | 0.26 |
| 10 | PEG-pGlu(Bn):DOTAP:DOPE = 1.25:1:1 | 2.06 |
| C3 | DOTAP:DOPE = 1:1 | 60.7 |

As shown in Table 2, the particulate compositions 3 to 10 had smaller absolute values of the zeta potential compared to the comparative particulate composition C3 which contained no block copolymer units. In the particulate compositions 3 to 10, the absolute values of the zeta potential became smaller as the weight ratio of the block copolymer units to the charged lipid became higher. This result means that the outer surface of the particulate compositions 3 to 10 were prevented from carrying charges resulting from the charged lipid. Assuming that the content of the charged lipids in the particulate compositions is constant, this result also means that the outer surface of the particles become less likely to carry charges resulting from the charged lipids, as the density of the area constituted by the hydrophilic polymer-chain segments becomes higher.

[Evaluation 1c: Evaluation of Aggregation in Blood]

Using the particulate compositions 3 to 10 and the comparative particulate composition C3 as the particulate compositions, the absorbance of the samples A and B prepared as described above at a wavelength of 700 nm was determined using a plate reader (POWERSCAN HT, Dainippon Sumitomo Pharma Co., Ltd.) to calculate the aggregability in blood. When the calculated value was 0 or less, the aggregability in blood was set at 0. Table 3 shows this data and the absolute values of the zeta potential determined in Evaluation 1b, while FIG. 2 shows the relationship between the absolute value of zeta potential and the aggregability in blood.

TABLE 3

| Particulate composition | Degree of aggregation in blood | Zeta potential (mV) |
|---|---|---|
| None | 0.118 | — |
| 3 | 0.093 | 2.04 |
| 4 | 0.177 | 5.38 |
| 5 | 0.185 | 7.80 |
| 6 | 0.198 | 11.0 |
| 7 | 0 | 1.63 |
| 8 | 0 | 1.09 |
| 9 | 0.012 | 0.26 |
| 10 | 0.073 | 2.06 |
| C3 | 0.375 | 60.7 |

Figure 2:
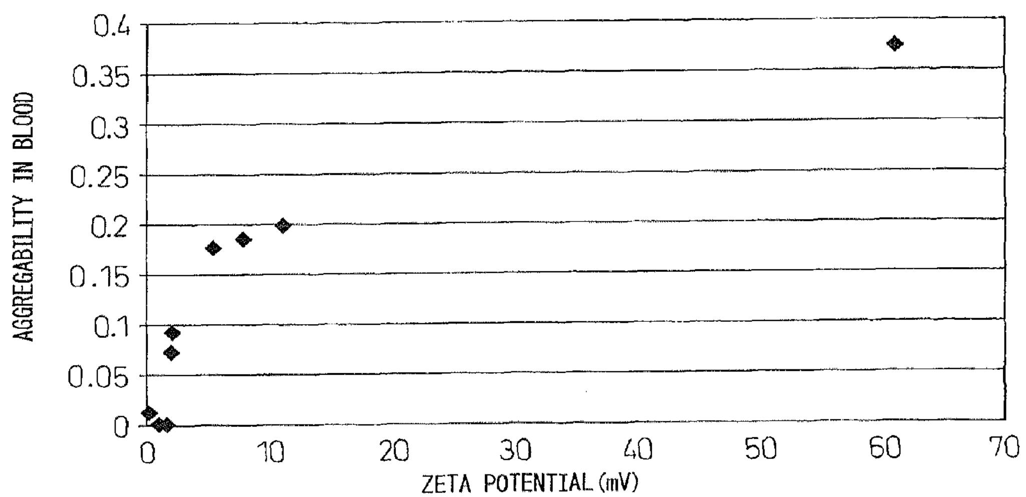
FIG. 2 is a graph showing the relationship between the absolute values of zeta potentials of particulate compositions measured in Evaluation 1b and the aggregability of the particulate compositions in blood measured in Evaluation 1c.

As can be seen from FIG. 2 and Table 3, the aggregability in blood was low when the absolute value of zeta potential of the particulate composition was 10 mV or lower, preferably 6 mV or lower, more preferably 3 mV or lower.

Example Group 2

Albumin (pH 7.4)-Encapsulating Particulate Composition

Example 2

Albumin-FITC (Sigma Aldrich), bovine-derived albumin labeled with FITC (fluorescein 5-isothiocyanate), was dissolved in 20 mM HEPES buffer (pH 7.4) to prepare a 10 mg/mL solution. 0.2 mL of this albumin solution was mixed with 0.5 mL of the particulate composition 1 (containing 40 mg/mL of PEG-PBLG and 4 mg/mL of DOTAP) and 0.5 mL of 20 mM HEPES buffer (pH 7.4), and allowed to stand overnight at 4° C. to thereby prepare an albumin-encapsulating particulate composition. The average particle size of the particulate composition measured by dynamic light scattering was 98.7 nm. Albumin is a biomacromolecule that has an isoelectric point (PI) of about 4.8 and thus exhibits an anionic character at pH 7.4.

Comparative Example 2-1

An albumin-encapsulating particulate composition was prepared in the same manner as in Example 2 except that the particulate composition 1 was replaced with the particulate composition 2 (containing 40 mg/mL of PEG-PBLG and 4 mg/mL of PA). The average particle size of the particulate composition measured by dynamic light scattering was 91.6 nm.

Comparative Example 2-2

An albumin-encapsulating particulate composition was prepared in the same manner as in Example 2 except that the particulate composition 1 was replaced with the comparative particulate composition C1 (containing 40 mg/mL of PEG-PBLG). The average particle size of the particulate composition measured by dynamic light scattering was 118 nm.

Comparative Example 2-3

An albumin-encapsulating particulate composition was prepared in the same manner as in Example 2 except that the particulate composition 1 was replaced with the comparative particulate composition C2 (containing 40 mg/mL of PEG-PBLG and 2 mg/mL of DOPE). The average particle size of the particulate composition measured by dynamic light scattering was 119 nm.

[Evaluation 2a: Evaluation of Retention of Albumin by Ultracentrifugation]

Forty μL each of the solutions of the albumin-encapsulating particulate compositions prepared in Example 2 and Comparative Examples 2-1 to 2-3 mixed with 360 μL of 10 mM HEPES buffer (pH 7.4) was ultracentrifuged at 100,000× g, 4° C. with an ultracentrifuge (Optima MAX Ultracentrifuge, Beckman Coulter). The fluorescence intensity of albumin-FITC in the supernatant was measured using a plate reader (POWERSCAN HT, manufactured by Dainippon Sumitomo Pharma Co., Ltd.) (excitation wavelength: 485 nm; fluorescence wavelength: 528 nm) to determine the retaining rate of albumin in the particulate composition based on the following equation (1).

$$(\text{Retaining rate})=(A-B)\times 100/A \qquad \text{Equation (1)}$$

A: Fluorescence intensity of albumin-FITC added to the particulate composition

B: Fluorescence intensity of albumin-FITC in the supernatant

TABLE 4

| | Particulate composition used | pH | Retaining rate of albumin-FITC (%) |
|---|---|---|---|
| Example 2 | 1 | 7.4 | 94.0 |
| Comparative Example 2-1 | 2 | 7.4 | 0 |
| Comparative Example 2-2 | C1 | 7.4 | 0 |
| Comparative Example 2-3 | C2 | 7.4 | 0 |

As shown in Table 4, as much as 94% of albumin was retained in the particles after centrifugation in Example 2, whereas in Comparative Examples 2-1 to 2-3 almost no albumin was present in the particles after centrifugation.

[Evaluation 2b: Evaluation of Albumin Retention by Gel Filtration Chromatography]

One mL each of the solutions of the albumin-encapsulating particles prepared in Example 2 and Comparative Example 2-1 was analyzed by gel filtration chromatography using Sepharose CL-4B. The eluate was collected in fractions, and the fluorescence intensity of the albumin-FITC contained in each fraction was measured using a plate reader (POWERSCAN HT, manufactured by Dainippon Sumitomo Pharma Co., Ltd.) (excitation wavelength: 485 nm; fluorescence wavelength: 528 nm). As the eluent, 10 mM HEPES buffer (pH 7.4) to which 150 mM sodium chloride has been added was used.

Figure 3:
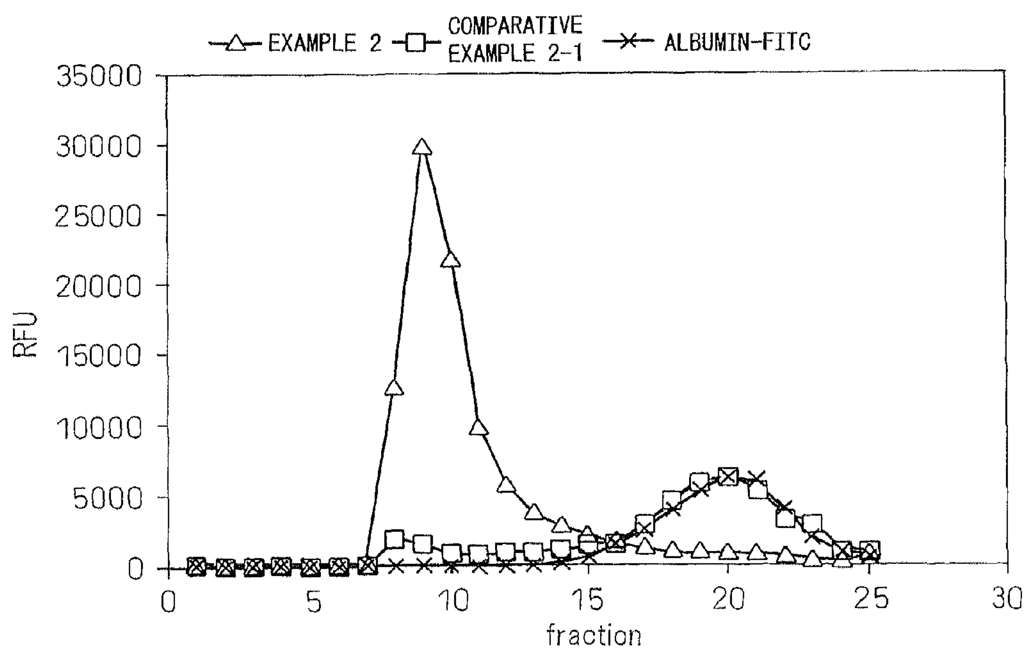
FIG. 3 is a graph showing fluorescence intensities of albumin-FITC measured in Evaluation 2b.

FIG. 3 is a graph showing the results of measurement. As shown in FIG. 3, elution peaks were observed in albumin per se and in fractions around fraction 20 in Comparative Example 2-1, whereas in Example 2 elution peaks were observed in fractions around fraction 10. This means that Example 2 has a better ability of retaining albumin in the particles compared to Comparative Example 2-1.

Example Group 3

Dextran-Encapsulating Particulate Composition

Example 3

Dextran-FITC (Sigma Aldrich), which is FITC-labelled dextran with an average molecular weight of 20000, was dissolved in 20 mM HEPES buffer (ph 7.4) to prepare a 10 mg/mL solution. 0.2 mL of this dextran solution was mixed with 0.5 mL of the particulate composition 1 (containing 40 mg/mL of PEG-PBLG and 4 mg/mL of DOTAP) and 0.5 mL of 20 mM HEPES buffer (pH 7.4), and allowed to stand overnight at 4° C. to thereby prepare a dextran-encapsulating particulate composition. The average particle size of the particulate composition measured by dynamic light scattering was 77.6 nm. Dextran is a biomacromolecule that exhibits an anionic character at pH 7.4.

Comparative Example 3-1

A dextran-encapsulating particulate composition was prepared in the same manner as in Example 3 except that the particulate composition 1 was replaced with the particulate composition 2 (containing 40 mg/mL of PEG-PBLG and 4 mg/mL of PA). The average particle size of the particulate composition measured by dynamic light scattering was 95.4 nm.

Comparative Example 3-2

A dextran-encapsulating particulate composition was prepared in the same manner as in Example 3 except that the particulate composition 1 was replaced with the comparative particulate composition C1 (containing 40 mg/mL of PEG-PBLG). The average particle size of the particulate composition measured by dynamic light scattering was 119 nm.

Comparative Example 3-3

A dextran-encapsulating particulate composition was prepared in the same manner as in Example 3 except that the particulate composition 1 was replaced with the comparative particulate composition C2 (containing 40 mg/mL of PEG-PBLG and 4 mg/mL of DOPE). The average particle size of the particulate composition measured by dynamic light scattering was 119 nm.

[Evaluation 3: Evaluation of Retention of Dextran by Ultracentrifugation]

For 40 μL each of the solutions of the dextran-encapsulating particulate compositions prepared in Example 3 and Comparative Examples 3-1 to 3-3, the fluorescence intensity of dextran-FITC in the supernatant was measured in a similar manner to the Evaluation 2a to determine the retaining rate of albumin of the particulate composition based on the following equation (2).

$$(\text{Retaining rate})=(A'-B')\times 100/A' \qquad \text{Equation (2)}$$

A': Fluorescence intensity of dextran-FITC added to the particulate composition

B: Fluorescence intensity of dextran-FITC in the supernatant

TABLE 5

| | Particulate composition used | pH | Retaining rate of dextran-FITC (%) |
|---|---|---|---|
| Example 3 | 1 | 7.4 | 38.67 |
| Comparative Example 3-1 | 2 | 7.4 | 6.24 |
| Comparative Example 3-2 | C1 | 7.4 | 2.39 |
| Comparative Example 3-3 | C2 | 7.4 | 4.03 |

As shown in Table 5, nearly 40% of dextran was retained in the particles after centrifugation in Example 3, whereas in Comparative Example 3-1 and 3-3 almost no albumin was present in the particles after centrifugation.

Example Group 4

Albumin (pH 3.3)-Encapsulating Particulate Composition

Example 4

Albumin (bovine-derived, Sigma Aldrich) was dissolved in 50 mM glycine buffer (pH 3) to prepare a 1 mg/mL solution. Two mL of this albumin solution was mixed with 0.5 mL of the particulate composition 2 (containing 40 mg/mL of PEG-PBLG and 4 mg/mL of PA) and 0.5 mL of 20 mM HEPES buffer (pH 7.4), and allowed to stand overnight at 4° C., pH 3.3 to thereby prepare an albumin-encapsulating particulate composition. The average particle size of the particulate composition measured by dynamic light scattering was 78.8 nm. Albumin exhibits a cationic character at pH 3.3.

Comparative Example 4-1

An albumin-encapsulating particulate composition was prepared in the same manner as in Example 4 except that the particulate composition 2 was replaced with the particulate composition 1 (containing 40 mg/mL of PEG-PBLG and 4 mg/mL of DOTAP). The average particle size of the particulate composition measured by dynamic light scattering was 95.1 nm.

Comparative Example 4-2

An albumin-encapsulating particulate composition was prepared in the same manner as in Example 4 except that the particulate composition 2 was replaced with the comparative particulate composition C1 (containing 40 mg/mL of PEG-PBLG). The average particle size of the particulate composition measured by dynamic light scattering was 115 nm.

Comparative Example 4-3

An albumin-encapsulating particulate composition was prepared in the same manner as in Example 4 except that the particulate composition 2 was replaced with the comparative particulate composition C2 (containing 40 mg/mL of PEG-PBLG and 1 mg/mL of DOPE). The average particle size of the particulate composition measured by dynamic light scattering was 120 nm.

[Evaluation 4: Evaluation of Albumin Retention by Ultracentrifugation]

400 μL each of the solutions of the albumin-encapsulating particulate compositions prepared in Example 4 and Comparative Examples 4-1 to 4-3 was ultracentrifuged for 1 hour at 100,000×g, 4° C. with an ultracentrifuge (Optima MAX Ultracentrifuge, Beckman Coulter). The concentration of albumin in the supernatant was determined using the protein determination kit BCA Protein Assay (Pierce) to determine the retaining rate of albumin in the particulate composition based on the following Equation (3).

$$(\text{Retaining rate})=(A''-B'')\times 100/A'' \qquad \text{Equation (3)}$$

A": Concentration of albumin added to the particulate composition

B": Concentration of albumin in the supernatant

TABLE 6

| | Particulate composition used | pH | Retaining rate of albumin (%) |
|---|---|---|---|
| Example 4 | 2 | 3.3 | 94.75 |
| Comparative Example 4-1 | 1 | 3.3 | 49.85 |
| Comparative Example 4-2 | C1 | 3.3 | 42.86 |
| Comparative Example 4-3 | C2 | 3.3 | 55.39 |

As shown in Table 6, over 94% of albumin was retained in the particles after centrifugation in Example 4, whereas in Comparative Examples 4-1 and 4-3 the retaining rate of albumin after centrifugation was not as high as in Example 4.

Example Group 5 siRNA-Encapsulating Particulate Composition

Example 5

According to the procedure shown below, each particulate composition was subjected to encapsulation treatment of siRNA.

For the particulate compositions 3 to 6 and the comparative particulate composition C3, encapsulation treatment was carried out as follows. siRNA was dissolved into 10 mM HEPES buffer (pH7.4) to prepare 20 μM siRNA solution. To 250 μL of this siRNA solution, 250 μL of the particulate composition of which concentration has been adjusted so as to satisfy the charge ratio (+/−) of interest was added, and after mixing, it was allowed to stand at 4° C. for 2 hours to effect the encapsulation treatment of siRNA into the particulate composition. The "charge ratio (+/−)" indicates [the concentration of cationic groups of the cationic lipid contained in the particulate composition]/[the concentration of the phosphoric group in the nucleic acid]. For the particulate compositions 7 to 10, 279 μL of the particulate composition was added to 100 μL of 100 μM aqueous siRNA solution, and after mixing, it was allowed to stand at 4° C. for 2 hours to carry out the encapsulation treatment of siRNA into the particulate composition. The charge ratio (+/−) of the siRNA-encapsulating particulate composition thus prepared is 8. The siRNA-encapsulated particulate compositions prepared from the particulate compositions 7 to 10 were subjected to the freezing-drying operation in a conventional manner to form a stock, and then dissolved into water again, and subjected to the measurements explained below.

In each of the Examples described in the present description, siRNA was selected from the ones explained below, all of which are available from Nippon EGT Co., Ltd.

siRNA(Luc): Designed to target a sea firefly luciferase gene, this siRNA is composed of a sense strand of 5'-CUUACGCUGAGUACUUCGAdTdT-3' (SEQ ID NO:1) and an antisense strand of 5'-UCGAAGUACUCAGCGUAAGdTdT-3' (SEQ ID NO:2) double-stranded in a conventional manner.

siRNA(Plk1): Designed to target the human Plk1 (Polo-like kinase 1) gene, this siRNA is composed of a sense strand of 5'-CCAUUAACGAGCUGCUUAAdTdT-3' (SEQ ID NO:3) and an antisense strand of 5'-UUAAGCAGCUCGUUAAUGGdTdT-3' (SEQ ID NO:4) double-stranded in a conventional manner. The Plk1 gene is a kinase which plays a role in the M phase of cell division. SiRNA(Plk1) induces apoptosis when transfected into the cell.

F-siRNA(Luc): This siRNA is formed in the same manner as siRNA(Luc) except that the antisense strand of SEQ ID NO:2 is Cy3-labeled at the 5' end (5'-Cy3-UCGAAGUACUCAGCGUAAGdTdT-3').

[Evaluation 5a]

In Evaluation 5a, the particulate composition 4 and the particulate composition 6 as the particulate composition and siRNA(Luc) as the siRNA were used, and were subjected to the siRNA-encapsulation treatment so as to obtain the charge ratio of 0.5, 1, 2, 4 and 8 in the method described in Example 5. The encapsulation rate of siRNA in each particulate composition after the encapsulation treatment was analyzed by electrophoresis as described below. Each particulate composition containing 100 ng of siRNA was loaded to a polyacrylamide gel (Novex 20% TBE Gel, Invitrogen), which was then subjected to electrophoresis using the TBE solution as the electrophoresis buffer under the condition of an applied voltage of 100 V and a migration time of 1 hour. As the control, 100 ng of siRNA was run simultaneously. After the electrophoresis was complete, the gel was stained with a development reagent SYBR™ Green II (Invitrogen), and imaged using an image analyzing instrument Molecular Imager FX (Bio-Rad).

Figure 4:
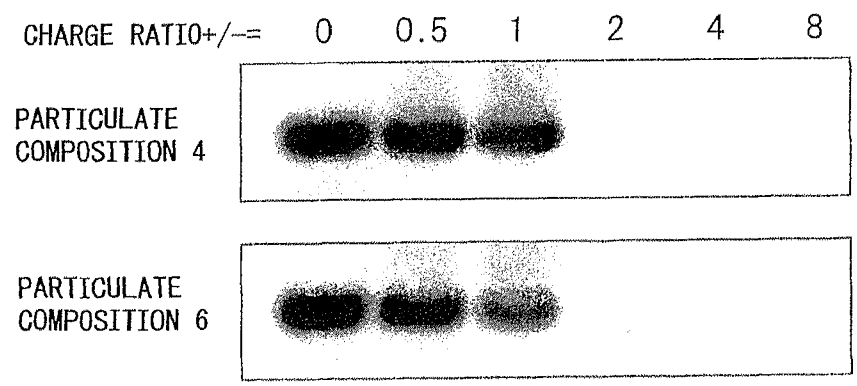

FIG. 4 shows the result of the electrophoresis in Evaluation 5a, in which a charge ratio of 0 means the control. As shown in FIG. 4, when the charge ratio was 2 or more, no bands derived from free siRNA were observed. This indicates that when the particulate composition 4 and the particulate composition 6 were used and the charge ratio was 2 or more, almost all siRNA could be encapsulated into the particulate compositions. Since the siRNA-encapsulated particulate compositions have a smaller degree of migration in electrophoresis compared to siRNA, bands derived from free siRNA cannot be detected in the corresponding migration lanes when siRNA is appropriately encapsulated.

[Evaluation 5b]

In Evaluation 5b, the particulate compositions 3 to 10 and the comparative particulate composition C3 as the particulate composition and siRNA(Luc) as the siRNA were used, and were subjected to the encapsulation treatment so as to obtain the charge ratio of 8 in the method described in Example 5. To the particulate compositions after the encapsulation treatment, 10 mM HEPES buffer (pH 7.4) was added to adjust the concentration of the charged lipid at 0.0 mg/mL. Using the light-scattering analyzer Zetasizer Nano ZS (Malvern Instruments), the zeta potential for these samples (800 μL) was determined. In the measurement, disposable capillary cells (DTS1060, Malvern Instruments) were used, and the temperature during measurement was set at 25° C.

TABLE 7

| Particulate composition used | Charge ratio (+/−) | Zeta potential (mV) | Zeta potential before treatment (mV) |
|---|---|---|---|
| 3 | 8 | 1.93 | 2.04 |
| 4 | 8 | 2.63 | 5.38 |
| 5 | 8 | 4.67 | 7.80 |
| 6 | 8 | 6.17 | 11.0 |
| 7 | 8 | 0.37 | 1.63 |
| 8 | 8 | 0.95 | 1.09 |
| 9 | 8 | 0.567 | 0.26 |
| 10 | 8 | 0.96 | 2.06 |
| C3 | 8 | 55.1 | 60.7 |

As shown in Table 7, the encapsulation-treated particulate compositions prepared using the particulate compositions 3 to 10 had markedly low absolute values of the zeta potential, suggesting that a lot of siRNA was encapsulated. Also as shown in Table 7, the degree of reduction of the zeta potential after the siRNA-encapsulation treatment was greater as the addition ratio of the charged lipid relative to the block copolymer units increased. This means that the greater the addition rate of the charged lipid is, the more siRNA can be encapsulated.

[Evaluation 5c: Evaluation of Activity on MDA-MB-231 Cells]

In Evaluation 5c, the particulate compositions 3 to 6 as the particulate composition and siRNA(Plk1) as the siRNA were used, and were subjected to the encapsulation treatment so as to obtain the charge ratio of 8 in the method described in Example 5. Using the siRNA-encapsulated particulate compositions, the following evaluation of activity on the MDA-MB-231 cells was carried out. As the inactive control sequence, siRNA(Luc) was used and run in a similar experiment.

[Activity Evaluation]

10 mM HEPES buffer (pH 7.4) was added to the siRNA-encapsulated particulate compositions to adjust the concentration of siRNA at 3 μM/mL. MDA-MB-231 cells derived from human breast cancer were plated in a 96-well plate at 2000 cells/well. Twenty four hours later, each siRNA-encapsulated particulate composition was added to the culture medium. The final concentration of siRNA in the medium was adjusted to be 300 nM, 100 nM, 33 nM and 11 nM. After further culturing for 96 hours, cell viability was evaluated using the Cell Counting Kit-8 (Dojindo Co., Ltd.).

Figure 5:
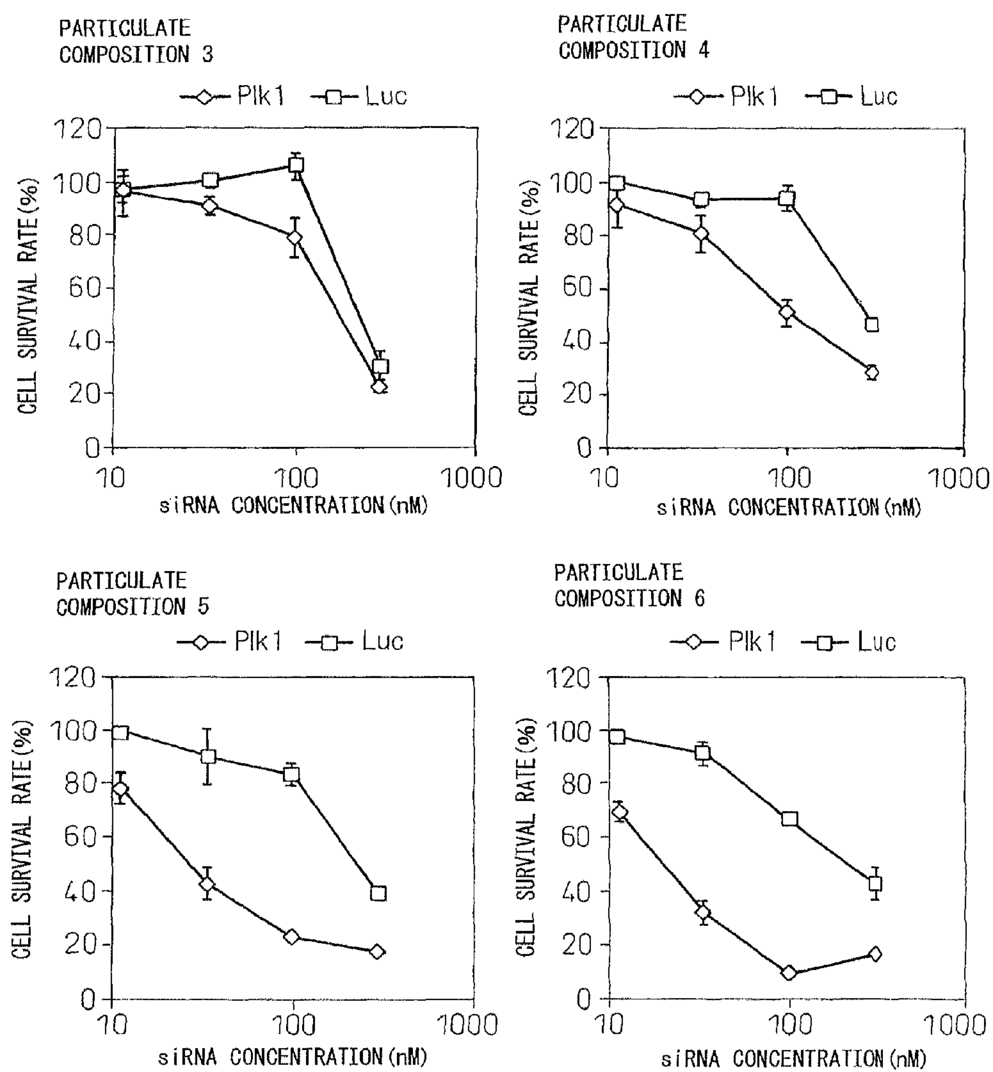
FIG. 5 indicates graphs for explaining anti-cancer activities of particulate compositions determined in Evaluation 5c.

FIG. 5 indicates graphs for explaining the result of this activity evaluation. As shown in FIG. 5, in the siRNA(Plk1)-encapsulating particulate compositions, cell counts were markedly reduced compared to the siRNA(Luc)-encapsulating particulate compositions.

[Evaluation 5d: Evaluation of Aggregation in Blood]

In Evaluation 5d, the particulate compositions 3 to 10 and the comparative particulate composition C3 as the particulate composition and siRNA(Luc) as the siRNA were used, and were subjected to the encapsulation treatment so as to obtain the charge ratio of 8 in the method described in Example 5. The absorbances of the samples A and B prepared as described above at a wavelength of 700 nm were determined using a plate reader (POWERSCAN HT, Dainippon Sumitomo Pharma Co., Ltd.) to calculate the aggregability in blood. When the calculated value was 0 or less, the aggregability in blood was set at 0.

Figure 6:
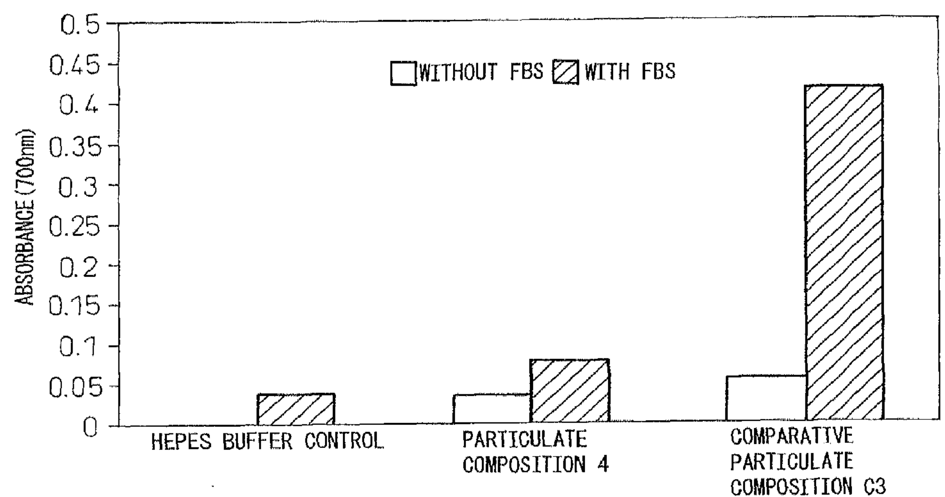
FIG. 6 is a graph for explaining the aggregability of particulate compositions in serum determined in Evaluation 5d.

FIG. 6 is a graph showing the absorbances of Measurement sample A (with FBS) and Measurement sample B (without FBS) for the encapsulation-treated particulate composition that used the particulate composition 4 and the encapsulation-treated particulate composition that used the comparative particulate composition C3. As shown in FIG. 6, the FBS treatment caused a significant increase in the absorbance in the encapsulation-treated particulate composition that used the comparative particulate composition C3. This indicates the occurrence of aggregation due to interactions with blood components. In the encapsulation-treated particulate composition (siRNA-encapsulated particulate composition) that used the particulate composition 4, almost no increase in absorbance due to the FBS treatment was observed.

The graph of FIG. 7 and Table 8 (shown below) show the relationship between the absolute values of zeta potential of the encapsulation-treated particulate compositions measured in Evaluation 5b and the aggregability in blood of the encapsulation-treated particulate compositions measured in Evaluation 5d.

TABLE 8

| Particulate composition used | Aggregation in blood | Zeta potential (mV) |
|---|---|---|
| None | 0.118 | — |
| 3 | 0.092 | 1.93 |
| 4 | 0.132 | 2.63 |
| 5 | 0.142 | 4.67 |
| 6 | 0.153 | 6.17 |
| 7 | 0 | 0.37 |
| 8 | 0 | 0.95 |
| 9 | 0 | 0.57 |
| 10 | 0 | 0.96 |
| C3 | 0.292 | 55.1 |

Figure 7:
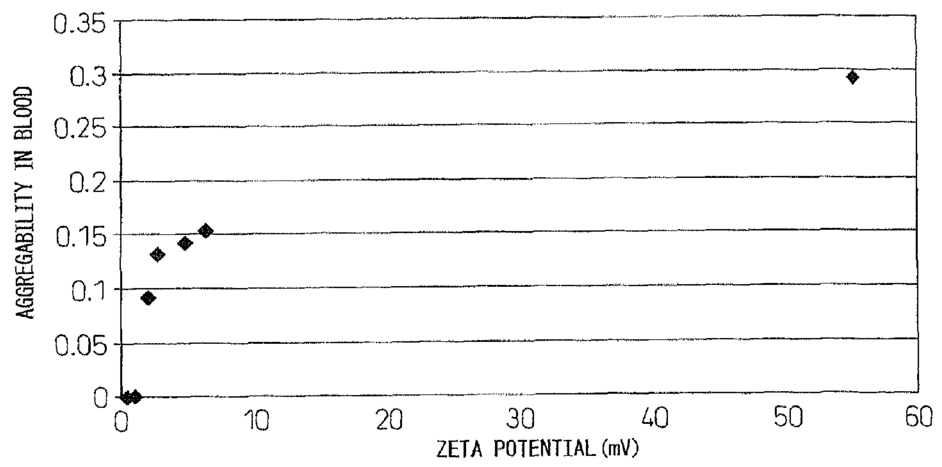
FIG. 7 is a graph showing the relationship between the absolute values of zeta potentials of particulate compositions measured in Evaluation 5b and the aggregability of particulate compositions in blood measured in Evaluation 5d.

As shown in FIG. 7 and Table 8, the encapsulation-treated particulate compositions had a markedly low aggregability in blood when the absolute values of the zeta potential thereof were 5 mV or lower, 3 mV or lower, furthermore 2 mV or lower, and specifically 1 mV or lower.

[Evaluation 5e: Evaluation of Remaining Rate in Blood]

In Evaluation 5e, the particulate compositions 3 to 10 as the particulate composition and F-siRNA(Luc) as the siRNA were used, and were subjected to the encapsulation treatment of siRNA so as to obtain the charge ratio of 8 in the method described in Example 5. For the particulate composition 4, the encapsulation-treated of siRNA was also carried out so as to obtain the charge ratio of 1, 2 and 4. To the siRNA-encapsulated particulate compositions thus prepared, 3M aqueous sodium chloride solution was added at a volume ratio of 1/20 to prepare an isotonic solution (siRNA encapsulation-treated particulate composition sample) containing 150 mM sodium chloride. As the control, to a 10 μM siRNA solution prepared by dissolving F-siRNA(Luc) into a 10 mM HEPES buffer (pH 7.4), a 3M aqueous sodium chloride solution was added at a volume ratio of 1/20 to prepare an isotonic solution (siRNA single sample) containing 150 mM sodium chloride. The siRNA-encapsulated particulate composition samples and the siRNA single sample were administered to Balb/c mice (prepared from Charles River Laboratories Japan, Inc.) via the tail vein, and 200 μL of blood was collected via the inferior vena cava one hour after. The dosage of each sample for each mouse was determined so as for the ratio of F-siRNA to the weight of the mouse to be 1 mg/kg.

The blood collected from each of the individuals that received a sample derived from the particulate compositions 3 to 6 was centrifuged with 2000×g at 4° C. for 10 minutes, and 80 μL of plasma was collected from the supernatant. The plasma was measured for fluorescence intensity using a plate reader (POWERSCAN HT, manufactured by Dainippon Sumitomo Pharma Co., Ltd.) (excitation wavelength: 485 nm; fluorescence wavelength: 528 nm) to determine the quantity of F-siRNA circulating in blood. The blood collected from each of the individuals that received a sample derived from the particulate compositions 7 to 10 was centrifuged with 2000×g at 4° C. for 10 minutes, and 100 μL of plasma was collected from the supernatant. To the plasma, one mL of Sepasol RNA I (Nakalai Tesque) was added, vortex-mixed, and allowed to stand for 5 minutes. 200 μL of chloroform was added thereto, mixed by inversion, and allowed to stand for 3 minutes. The solution was centrifuged with 2000×g at 4° C. for 10 minutes, and 300 μL of the supernatant prepared was measured for fluorescence intensity using a plate reader (POWERSCAN HT, manufactured by Dainippon Sumitomo Pharma Co., Ltd.) (excitation wavelength: 485 nm; fluorescence wavelength: 528 nm) to determine the quantity of F-siRNA circulating in blood.

TABLE 9

| Particulate composition used | Charge ratio (+/−) | Zeta potential (mV) | Remaining rate in blood relative to the dosage of F-siRNA (%) |
|---|---|---|---|
| None (single F-siRNA) | — | — | <0.4 |
| 3 | 8 | 1.93 | 5.2 |
| 4 | 8 | 2.63 | 4.3 |
| 5 | 8 | 4.67 | 3.0 |
| 6 | 8 | 6.17 | 2.3 |
| 7 | 8 | 0.37 | 37.9 |
| 8 | 8 | 0.95 | 0.9 |
| 9 | 8 | 0.57 | 15.5 |
| 10 | 8 | 0.96 | 2.8 |

TABLE 10

| Particulate composition used | Charge ratio (+/−) | Remaining rate in blood relative to the dosage of F-siRNA (%) |
|---|---|---|
| 4 | 1 | 0.46 |
| 4 | 2 | 1.2 |
| 4 | 4 | 3.6 |
| 4 | 8 | 4.3 |

As shown in Table 9, 0.9% or more of F-siRNA remained in blood for the siRNA-encapsulated particulate compositions prepared using the particulate compositions 3 to 10. The remaining rate of F-siRNA was higher as the weight ratio of the block copolymer units to the charged lipid becomes greater in the siRNA-encapsulated particulate compositions. This means that when the content of the charged lipid in the particulate composition is assumed to be constant, the period of retaining the drug in blood becomes longer as the density of the region formed by the hydrophilic polymer-chain segments becomes increased. Also, the lower the absolute value of zeta potential of the sample, the remaining rate of F-siRNA becomes higher. For example, the remaining rate of F-siRNA of a sample prepared by using the particulate composition 7 having the absolute value of zeta potential of 0.37 mV was 37.9%, while the remaining rate of F-siRNA of a sample prepared by using the particulate composition 9 having the absolute value of zeta potential of 0.57 mV was 15.5%. As shown in Table 10, the remaining rate of F-siRNA was higher as the charge ratio in the siRNA-encapsulated particulate compositions became higher. This means that the more the amount of the charged lipid added is, the longer the period becomes in which the particles can retain the drug in blood.

For a sample prepared by carrying out the encapsulation treatment so as to obtain the charge ratio of 1.5 using the particulate composition 6 as the particulate composition and siRNA(Luc) as the siRNA in the method described in Example 5, the zeta potential was measured in the method described in Evaluation 5b. The absolute value was 0.36 mV, which was almost equal to the sample prepared using the particulate composition 7. However, for a sample (zeta potential: 0.36 mV) prepared by carrying out the encapsulation treatment on the particulate composition 6 using F-siRNA (Luc) as the siRNA in the method described in Evaluation 5e, the remaining rate in blood was evaluated, and the amount of F-siRNA remaining in blood was found to be 0.91%. Thus, while the sample prepared using the particulate composition 7 had about the same absolute value of the zeta potential as the sample prepared using the particulate composition 6, it had a markedly excellent retaining rate of the encapsulated drug in blood. Therefore, by forming the particulate composition with anionic polymers, the retaining rate of the encapsulated drug in blood can be significantly enhanced compared to when the particulate composition was formed with neutral polymers.

[Evaluation 5f: Evaluation of Organ Migration]

In Evaluation 5f, the encapsulation treatment of siRNA was carried out using the particulate composition 3 and the comparative particulate composition 3 as the particulate composition and F-siRNA(Luc) as the siRNA so as to obtain the charge ratio of 8 in the method described in Example 5. To the encapsulation-treated particulate compositions thus prepared, a 3M aqueous sodium chloride solution was added at a volume ratio of 1/20 to prepare an isotonic solution (encapsulation-treated particulate composition sample) containing 150 mM sodium chloride. MDA-MB-231 cells derived from human breast cancer were transplanted to Balb/c nude mice (female, 5 week-old, prepared from Charles River Laboratories Japan, Inc.). To mice of which tumor size became 200 $mm^2$ or greater four weeks later, the encapsulation-treated particulate composition sample was administered. The amount of F-siRNA given was adjusted to be 1 mg/kg of mouse body weight. At 10, 60 and 180 minutes after the administration, 50 to 100 μg of each organ was collected, to which one mL each of the RNA extraction reagent Sepasol RNA I (Nakalai Tesque) was added, and homogenized. To 500 μL of each homogenate, 100 μL of chloroform was added, and centrifuged at 4° C., 5200 G for 10 minutes. Then, 200 μL of the supernatant prepared was measured for fluorescence intensity using a plate reader (POWERSCAN HT, manufactured by Dainippon Sumitomo Pharma Co., Ltd.) (excitation wavelength: 485 nm; fluorescence wavelength: 528 nm) to determine the quantity of F-siRNA that migrated into each organ.

TABLE 11

| Particulate composition used | Time after administration (min) | Migration rate (%) Blood | Tumor | Liver | Lung | Kidney | Spleen |
|---|---|---|---|---|---|---|---|
| 4 | 10 | 10.8 | 0.3 | 8.1 | 15.0 | 2.3 | 19.0 |
| | 60 | 0.9 | n.d. | 3.8 | 0.7 | 0.6 | 9.9 |
| | 180 | 0.8 | n.d. | 0.7 | 0.3 | 0.1 | 1.7 |
| C3 | 10 | 0.3 | n.d. | 0.6 | 178.9 | 0.7 | 0.5 |
| | 60 | 0.3 | n.d. | 1.2 | 103.1 | 0.2 | 0.4 |
| | 180 | 0.2 | n.d. | 0.5 | 56.7 | n.d. | n.d. |

* The migration rate indicates the ratio (%) of the determined value of F-siRNA per g of the organ to the amount administered of F-siRNA per each mouse. "n.d." stands for "not detected".

Figure 8:
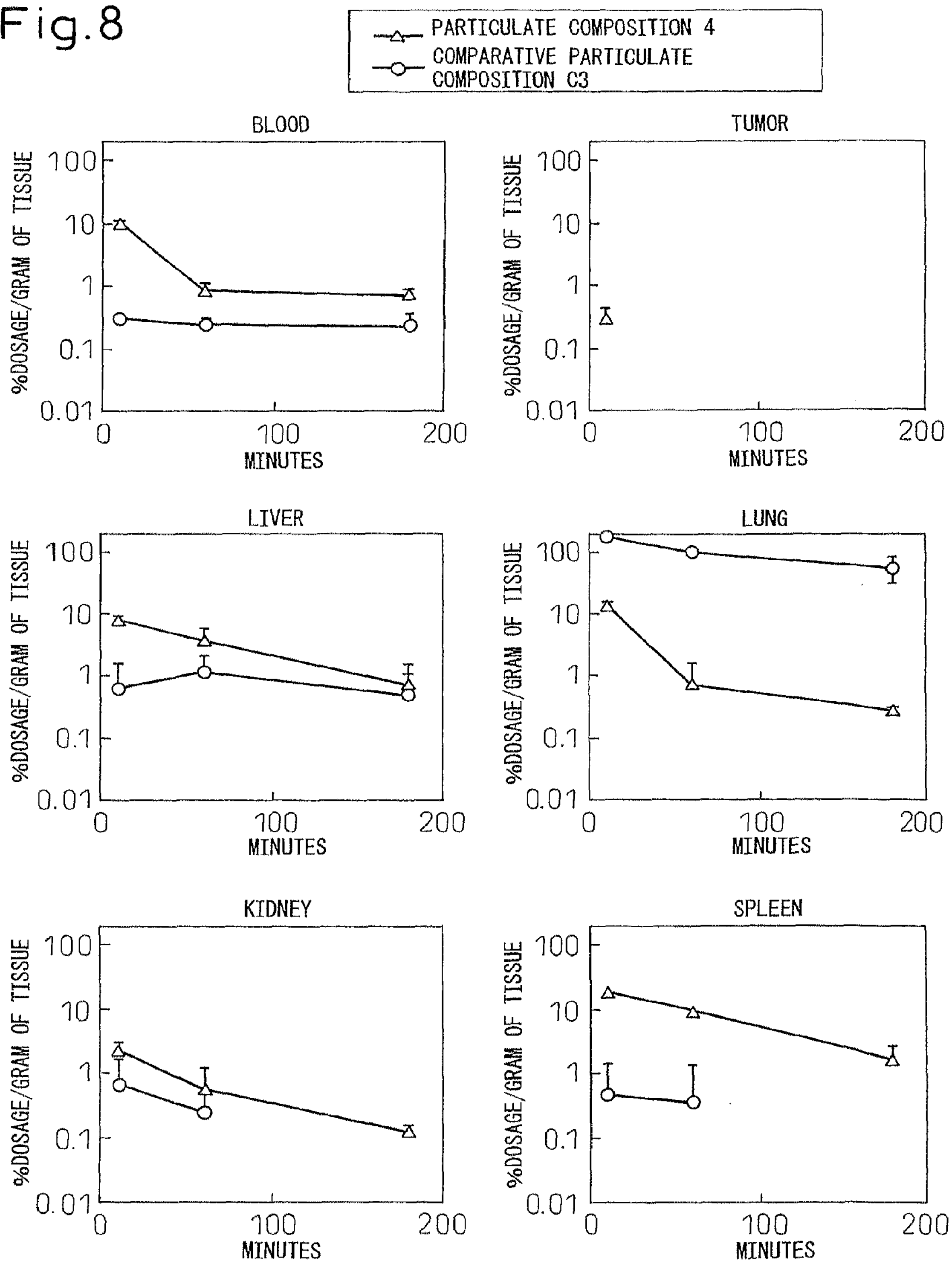
FIG. 8 indicates graphs for explaining drug migration to organs determined in Evaluation 5f.

FIG. 8 indicates graphs for explaining the drug migration into organs investigated in Evaluation 5f. As shown in FIG. 7 and Table 11, the encapsulation-treated particulate composition prepared using the comparative particulate composition C3 rapidly disappeared from blood, and its significant accumulation in the lung was observed. On the other hand, the siRNA-encapsulated particulate composition prepared using the particulate composition 4 remained in blood for a much longer period of time, and its migration into the tumor was also observed.

INDUSTRIAL APPLICABILITY

The particulate composition of the present invention can be used as a drug carrier for preparing a drug-encapsulated pharmaceutical composition, whereby the drug (specifically a polymer compound) can more effectively be retained in vivo and protected against decomposition or excretion, and the drug can be delivered to the affected area while maintaining its activity. Furthermore, aggregation of the drug carrier due to interaction with blood components can be avoided. These features would highly improve the drug availability and thereby serve to reduce the dosage significantly, leading to improvement in medicoeconomics and effective expression of physiological effects. The reduction in the dosage would also be useful for controlling side effects, such as induction of immune responses to, e.g., proteins and nucleic acids, as well as adverse effects on the blood coagulation system.

The invention claimed is:

1. A particulate composition for encapsulating a drug therein, comprising:

a block copolymer unit having a hydrophobic polymer-chain segment and a hydrophilic polymer-chain segment, a plurality of the block copolymer units being arranged radially with the hydrophobic polymer-chain segments radially inside and the hydrophilic polymer-chain segments radially outside; and a plurality of charged lipids, each of which carries a charge opposite to the charge of the drug to be encapsulated in the composition such that the drug is to be retained within the particle via electrostatic binding with at least one of the charged lipids, the charged lipids being attracted to the hydrophobic polymer-chain segment, whereby the outer surface of the particle is prevented from being charged to attract a substance which has a charge opposite to the charge of the charged lipids, wherein the particulate composition is applied to a drug being a biomolecule selected from the group consisting of proteins and nucleic acids, and wherein the hydrophilic polymer-segment is a polyethylene glycol chain and the hydrophobic polymer-chain segment is an anionic polyamino acid polymer-chain segment, wherein the weight ratio of the weight of the block copolymer units to the weight of the charged lipids is 1.0 or higher, and wherein the absolute value of zeta potential of the particulate composition is limited to 15 mV or lower, the zeta potential being measured when the composition is added to 10 mM HEPES buffer (pH 7.4) in such an amount that the ratio of the total charged lipids to the buffer solution is 0.1 mg/ml.

2. The particulate composition according to claim 1, wherein the charged lipids are not arranged contiguously to one another along the circumference of the particulate composition, but at least a portion of the charged lipids are arranged to intervene between the adjacent block copolymer units along the circumference of the particulate composition, whereby the adjacent charged lipids along the circumference of the particulate composition are separated by the block copolymer units and prevented from being in contact with one another.

3. The particulate composition according to claim 1, wherein the composition is prevented from aggregating in blood.

4. The particulate composition according to claim 3, wherein the absolute value of zeta potential of the particulate composition is limited to 3 mV or lower whereby the composition is further prevented from aggregating in blood.

5. A pharmaceutical composition comprising: a particulate composition according to claim 1; and a drug which is encapsulated in the particulate composition and carries a charge opposite to the charge of the charged lipids, wherein the drug includes a biomolecule selected from the group consisting of proteins and nucleic acids.

6. The pharmaceutical composition according to claim 5, wherein the absolute value of zeta potential of the particulate composition is limited to 10 mV or lower whereby the composition is prevented from aggregating in blood, the zeta potential being measured when the composition is added to 10 mM HEPES buffer (pH 7.4) in such an amount that the ratio of the total charged lipids to the buffer solution is 0.1 mg/ml.

7. The pharmaceutical composition according to claim 6, wherein the absolute value of zeta potential of the particulate composition is limited to 2 mV or lower whereby the composition is further prevented from aggregating in blood.

8. The pharmaceutical composition according to claim 5, wherein the hydrophobic polymer-chain segment is formed with the anionic polyamino acid polymer-chain segment whereby the retaining rate of the drug is enhanced.

* * * * *